United States Patent
Styczynski et al.

(12) 
(10) Patent No.: US 6,299,865 B1
(45) Date of Patent: *Oct. 9, 2001

(54) REDUCTION OF HAIR GROWTH

(76) Inventors: Peter Styczynski, 3709 Roop Rd., New Windsor, MD (US) 21776; Gurpreet S. Ahluwalia, 10804 Barnwood La., Potomac, MD (US) 20854

(*) Notice: Subject to any disclaimer, the term of this patent is extended or adjusted under 35 U.S.C. 154(b) by 0 days.

This patent is subject to a terminal disclaimer.

(21) Appl. No.: 09/561,657

(22) Filed: May 2, 2000

(51) Int. Cl.[7] ............ A01N 43/16; A01N 43/78; A01N 59/16; A61K 31/35; A61K 31/425; A61K 33/24; A61K 7/06; A61K 31/74; A61K 33/26

(52) U.S. Cl. ............ 424/70.1; 424/650; 424/401; 424/78.02; 424/646; 514/456; 514/368; 514/880

(58) Field of Search ............ 424/646, 650, 424/70.1, 78.02; 514/456, 368, 880

(56) References Cited

U.S. PATENT DOCUMENTS

| | | |
|---|---|---|
| 3,426,137 | 2/1969 | Philpitt et al. . |
| 4,039,669 | 8/1977 | Beylar et al. . |
| 4,139,638 | 2/1979 | Neri et al. . |
| 4,161,540 | 7/1979 | Neri et al. . |
| 4,191,775 | 3/1980 | Glen . |
| 4,192,860 | 3/1980 | Griffiths . |
| 4,269,831 | 5/1981 | Ferrari et al. . |
| 4,370,315 | 1/1983 | Greff et al. . |
| 4,439,432 | 3/1984 | Peat . |
| 4,439,439 | 3/1984 | Ballany et al. . |
| 4,490,354 | 12/1984 | Meriwether . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Breuer et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Haverhagen . |
| 5,300,284 | 4/1994 | Wiechers et al. . |
| 5,328,686 | 7/1994 | Shander et al. . |
| 5,362,748 | 11/1994 | Schwen et al. . |
| 5,364,885 | 11/1994 | Ahluwalia et al. . |
| 5,411,991 | 5/1995 | Shander et al. . |
| 5,444,090 | 8/1995 | Ahluwalia et al. . |
| 5,455,234 | 10/1995 | Ahluwalia et al. . |
| 5,468,476 | 11/1995 | Ahluwalia et al. . |
| 5,474,763 | 12/1995 | Shander et al. . |
| 5,480,645 * | 1/1996 | Della Valle et al. ........ 424/439 |
| 5,554,608 | 9/1996 | Ahluwalia et al. . |
| 5,556,645 | 9/1996 | Bockman et al. . |

(List continued on next page.)

FOREIGN PATENT DOCUMENTS

| | | |
|---|---|---|
| 0 113 397 A | 7/1984 | (EP) . |
| 0 413 528 A1 | 2/1991 | (EP) . |
| 0 532 219 A2 | 3/1993 | (EP) . |
| 1 458 349 | 12/1976 | (GB) . |
| WO 91/10437 | 7/1991 | (WO) . |
| WO 96/26712 | 9/1996 | (WO) . |
| WO 98/02134 | 1/1998 | (WO) . |
| WO 98/29086 | 7/1998 | (WO) . |
| WO 99/15136 | 4/1999 | (WO) . |
| WO 99/29288 | 6/1999 | (WO) . |
| WO 99/30679 | 6/1999 | (WO) . |
| WO 99/30680 | 6/1999 | (WO) . |
| WO 99/36067 | 7/1999 | (WO) . |
| WO 99/37277 | 7/1999 | (WO) . |
| WO 99/38474 | 8/1999 | (WO) . |
| WO 99/62465 | 12/1999 | (WO) . |
| WO 00/24368 | 5/2000 | (WO) . |

OTHER PUBLICATIONS

Tomita et al., "Skin–lightening cosmetic containing antihistaminics, mast cell degranulation inhibitors, cyclooxygenase inhibitors, or lipoxygenase inhibitors", Chem. Abs. 112:204493d, Jan. 1990.

Millan et al., "Biology of Human Alkaline Phosphatases with Special Reference to Cancer", Critical Reviews in Clinical Laboratory Sciences, vol. 32, pp. 1–39, 1995.

Handjiski et al., "Alkaline phosphatase activity and localization during the murine hair cycle", British Journal of Dermatology, vol. 131, pp. 303–310, 1994.

De Aspuru et al., "Effect of the Antiallergic Drug Disodium Cromoglycate and Various Derivatives on Alkaline Phosphatase", J. Enzyme Inhibition, vol. 8, pp. 87–95, 1994.

Boskey et al., "Gallium nitrate inhibits alkaline phosphatase activity in a differentiating mesenchymal cell culture", Bone and Mineral, vol. 20, pp. 179–192, 1993.

Cortizo et al., "Vanadium Compounds Their Action on Alkaline Phosphatase Activity", Biological Trace Element Research, vol. 41, pp. 331–339, 1994.

Weinberg et al., "Reconstitution of Hair Follicle Development In Vivo: Determination of Follicle Formation, Hair Growth, and Hair Quality by Dermal Cells", The J. of Invest. Derm. vol. 100, pp. 229–236, Mar. 1993.

Chen et al., "Characterization of a Cloned Human Dihydrotestosterone/Androstanediol UDP–Glucuronosyltransferase and Its Comparison to Other Steroid Isoforms", Biochemistry, vol. 32, No. 40, 10648–57, 1993.

(List continued on next page.)

*Primary Examiner*—Dameron L. Jones
*Assistant Examiner*—Lauren Q Wells
(74) *Attorney, Agent, or Firm*—Fish & Richardson P.C.

(57) ABSTRACT

Mammalian hair growth is reduced by applying to the skin an inhibitor of alkaline phosphatase other than cromoglycate or a salt thereof.

21 Claims, No Drawings

U.S. PATENT DOCUMENTS

| | | |
|---|---|---|
| 5,645,825 | 7/1997 | Hillebrand et al. . |
| 5,648,394 | 7/1997 | Boxall et al. . |
| 5,652,273 | 7/1997 | Henry et al. . |
| 5,674,477 | 10/1997 | Ahluwalia et al. . |
| 5,728,736 | 3/1998 | Shander et al. . |
| 5,776,442 | 7/1998 | Ahluwalia . |
| 5,824,665 | 10/1998 | Henry et al. . |
| 5,840,752 | 11/1998 | Henry et al. . |
| 5,908,867 | 6/1999 | Henry et al. . |
| 5,912,010 * | 6/1999 | Wille et al. ............... 424/449 |
| 5,939,458 | 8/1999 | Henry et al. . |
| 5,958,946 | 9/1999 | Styczynski et al. . |
| 5,962,466 | 10/1999 | Styczynski et al. . |
| 6,020,006 | 2/2000 | Styczynski et al. . |
| 6,037,326 | 3/2000 | Styczynski et al. . |
| 6,060,471 | 5/2000 | Styczynski et al. . |
| 6,093,748 | 7/2000 | Ahluwalia et al. . |
| 6,121,269 | 9/2000 | Henry et al. . |
| 6,150,400 * | 11/2000 | Nyirjesy et al. ............ 514/456 |

OTHER PUBLICATIONS

Michael R. Franklin, "Drug Metabolizing Enzyme Induction by Simple Diaryl Pydridines; 2–Substituted Isomers Selectively Increase Only Conjugation Enzyme Activities . . . ", Toxicology and Applied Pharmacology, 111, 1991.

J. Baron, "In situ sites for xenobiotic activation and detoxication: Implications for the differential susceptibility of cells to the toxic . . . ", Progress in Histo– and Cytochemistry, vol. 23, 1991.

Tephly et al., "UDP–glucuronosyltransferases: a family of detoxifying enzymes", TIPS Reviews, Jul. 1990.

Ritter et al., "Induction of Hepatic Oxidative and Conjugative Drug Metabolism in the Hamster by N– Substituted Imidazoles", Toxicology Letters, 36, pp. 51–59, 1987.

Andrew G. Messenger, "The Control of Hair Growth: An Overview", The Society for Investigative Dermatololgy, Inc., 1993.

Jose Millan, "Alkaline phosphatase as a reporter of cancerous transformation", Clinica Chimica Acta., vol. 209, pp. 123–129, 1992.

Hattori et al., "Biochemical Analysis of Hair Growth from the Aspects of Aging and Enzyme Activities", vol. 10, pp. 45–54, 1983.

Cyboron et al., "Activity of Epiphyseal Cartilage Membrane Alkaline Phosphatase and the Effects of Its Inhibitors at Physiological ph*", The Journal of Biological Chemical, vol. 257, pp. 4141–4146, 1982.

Lyne et al., "Asymmetric Distribution of Alkaline Phosphatase Activity in the Hair and Wool Follicles of Sheep*", The Journal of Investigative Dermatology, vol. 48, pp. 197–199, 1967.

* cited by examiner

REDUCTION OF HAIR GROWTH

BACKGROUND OF THE INVENTION

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Alkaline phosphatase is a widely distributed zinc-metalloenzyme that is thought to make a contribution to the maintenance of cellular homeostasis. Although the precise function for alkaline phosphatase in the maintenance of cellular homeostasis remains unclear, numerous physiological activities have been suggested for this enzyme. Such activities include controlling the levels of inorganic phosphate, regulation of inorganic phosphate transport, acting as a calcium-binding protein and a calcium-magnesium ATPase, and functioning as a tyrosine-specific phosphoprotein phosphatase.

In addition to its enzymatic activity, alkaline phosphatase levels have been used as diagnostic markers in the clinical evaluation of numerous diseases. For instance, alkaline phosphatase is used as a nonspecific indicator for cancer to characterize bone resorption patterns in individuals susceptible to osteoporosis.

Four alkaline phosphatase genes have been cloned and sequenced. In addition, their chromosomal locations have been determined and the regulation of these genes has been studied. Human alkaline phosphatases are encoded by a gene family including four loci. At the end of the long chromosome 2, bands q34–q37, are clustered three tissue specific alkaline phosphatase genes: intestinal, placental, and germ cell. A tissue nonspecific alkaline phosphatase gene is located at the end of the short arm of chromosome 1, bands p36.1–p34. The amino acid sequence homology for the tissue-specific enzymes is 90–98%, whereas the gnon-specific form is only 50–60% homologous with any of the specific forms.

Human alkaline phosphatase display a unique characteristic not seen in alkaline phosphatase from lower species (prokaryotic)—uncompetitive inhibition by certain L-amino acids (Millan, Clinica Chimica Acta. 209:123–129, 1992). For example, tryptophan, phenylalanine and leucine inhibit the tissue-specific form of alkaline phosphatase in a stereoselective fashion in that only the L-form is active. L-homoarginine acts as an inhibitor of the tissue nonspecific form of alkaline phosphatase in several species.

Inhibitors of mast cell degranulation interfere with the release of histamine from mast cells. Examples of inhibitors of mast cell degranulation include mycophenolic acid, bromoryptine, and cromoglycate.

SUMMARY OF THE INVENTION

The invention features reducing unwanted mammalian (including human) hair growth ) —particularly androgen-stimulated hair growth—by applying to the skin a composition including an inhibitor of alkaline phosphatase other than cromoglycate (or salts thereof) in an amount effective to reduce hair growth. The unwanted hair growth which is reduced may be normal hair growth, or hair growth that results from an abnormal or diseased condition.

The invention also features reducing unwanted mammal hair growth by reducing the amount of alkaline phosphatase enzyme protein in hair follicle cells. This can be accomplished by the use of agents such as antisense-oligonucleotides that are designed to bind specifically the alkaline phosphatase messenger-RNA. The latter molecule is responsible for the synthesis of alkaline phosphatase enzyme in cells.

Other features and advantages of the invention may be apparent from the description of the preferred embodiments thereof, and from the claims.

DESCRIPTION OF PREFERRED EMBODIMENTS

The preferred composition includes at least one inhibitor of alkaline phosphatase in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or hydroalcoholic solution. The composition may also be in the form of a shaving preparation or an after shave. The vehicle itself can be inert or it can possess cosmetic, physiological and/or pharmaceutical benefits of its own.

Inhibitors of alkaline phosphatase include uncompetitive inhibitors such as tetramisole ([±]-2,3,5,6-tetrahydro-6-phenyl-imidazo[2,1-b]thiazole]) and competitive inhibitors such as sodium orthovanadate. Other inhibitors of alkaline phosphatase include levamisole (L[−]-2,3,5,6-tetrahydro-6-phenyl-imidazo[2,1-b]thiazole]), vanadium nitrate, and gallium nitrate.

The composition may include more than one inhibitor of alkaline phosphatase. In addition, the composition may include one or more other types of hair growth reducing agents, such as those described in U.S. Pat. No. 4,885,289; U.S. Pat. No. 4,720,489; U.S. Pat. No. 5,132,293; U.S. Pat. No. 5,096,911; U.S. Pat. No. 5,095,007; U.S. Pat. No. 5,143,925; U.S. Pat. No. 5,328,686; U.S. Pat. No. 5,440,090; U.S. Pat. No. 5,364,885; U.S. Pat. No. 5,411,991; U.S. Pat. No. 5,648,394; U.S. Pat. No. 5,468,476; U.S. Pat. No. 5,475,763; U.S. Pat. No. 5,455,608; U.S. Pat. No. 5,674,477; U.S. Pat. No. 5,728,736; U.S. Pat. No. 5,652,273; WO 94/27586; WO 94/27563; and WO 98/03149, all of which are incorporated herein by reference.

The concentration of the inhibitor of alkaline phosphatase in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, olive oil, petroleum jelly, palmitic acid, oleic acid, and myristyl myristate. Solvents may include ethyl alcohol, isopropanol, acetone, diethylene glycol, ethylene glycol, dimethyl sulfoxide, and dimethyl formamide.

The composition also may include components that enhance the penetration of the inhibitors of alkaline phosphatase into the skin and/or to the site of action. Examples of penetration enhancers include urea, propan-2-ol, polyoxyethylene ethers, terpenes, cis-fatty acids (oleic acid, palmitoleic acid), acetone, laurocapram dimethyl sulfoxide, 2-pyrrolidone, oleyl alcohol, glyceryl-3-stearate, cholesterol, myristic acid isopropyl ester, and propylene glycol.

The composition also can be formulated to provide a reservoir within or on the surface of the skin to provide for a continual slow release of the inhibitor. The composition also may be formulated to evaporate slowly from the skin, allowing the inhibitor extra time to penetrate the skin.

The following are examples of compositions including an inhibitor of alkaline phosphatase.

EXAMPLE 1

A composition containing 10% by weight of tetramisole in a vehicle containing water 68%, ethanol 16%, propylene glycol 5%, dipropylene glycol 5%, benzyl alcohol 4%, and propylene carbonate 2%.

EXAMPLE 2

A composition containing 1% by weight of sodium orthovanadate in a vehicle containing water 68%, ethanol 16%, propylene glycol 5%, dipropylene glycol 5%, benzyl alcohol 4%, and propylene carbonate 2%.

EXAMPLE 3

A composition containing 10% by weight of tetramisole in a vehicle containing water 80.84%, glyceryl stearate 4.24%, polyethylene glycol 100-stearate 4.09%, cetearyl alcohol 3.05%, ceteareth-20 2.5%, mineral oil 2.22%, steryl alcohol 1.67%, and dimethicone 0.56%.

EXAMPLE 4

A composition containing 1% by weight of sodium orthovanadate in a vehicle containing water 80.84%, glyceryl stearate 4.24%, polyethylene glycol 100-stearate 4.09%, cetearyl alcohol 3.05%, ceteareth-20 2.5%, mineral oil 2.22%, steryl alcohol 1.67%, and dimethicone 0.56%.

EXAMPLE 5

Any one or more of the previous examples in combination with one or more of the following penetration enhancers: urea 2%, polyoxyethylene-4-lauryl ether (Brij-30; Laureth-4), 3-hydroxy-3,7,11-trimethyl-1,6,1-dodecatriene (nerolidol) and/or cis-9-octadecenoic (oleic acid).

The composition should be topically applied to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women suffering from hirsutism or other conditions. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Golden Syrian Hamster Assay

Male intact Golden Syrian hamsters are considered acceptable models for human beard hair growth in that they display oval shaped flank organs, one on each side, each about 8 mm. In major diameter. These organs produce fine light colored hair typical of the animal pelage found on the body. In response to androgens the flank organs produce dark coarse hair similar to male human beard hair. To evaluate the effectiveness of a composition including an inhibitor of alkaline phosphatase, the flank organs of each of a group of hamsters are depilated by applying a thioglycolate based chemical depilatory (Surgex) and/or shaved. To one organ of each animal 10 µl. of vehicle alone once a day is applied, while to the other organ of each animal an equal amount of vehicle containing an inhibitor of alkaline phosphatase is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster"assay. Preferred compositions provide a reduction in hair growth of at least about 15%, more preferably at least about 30%, and most preferably at least about 50% when tested in the Golden Syrian hamster assay. Examples 1 and 2 (described above) were tested in the Golden Syrian hamster assay; the results are provided in Table 1:

TABLE 1

| Composition | pH | Dose | Treated (mg) | Vehicle (mg) | Reduction |
|---|---|---|---|---|---|
| Example 1 | 5.0 | 10% | 1.11 ± .36 | 2.61 ± 29 | 62 ± 7 |
| Example 2 | 7.5 | 1% | 0.91 ± .10 | 1.58 ± .08 | 40 ± 8 |

Human Hair Follicle Growth Assay

Human hair follicles in growth phase (anagen) were isolated from face-lift tissue under a dissecting scope using a scalpel and watchmakers forceps. The skin was sliced into thin strips exposing 2–3 rows of follicles that could readily be dissected. Follicles were placed into 0.5 mL Williams E medium (Life Technologies, Gaithersburg, Md.) supplemented with 2 mm L-glutamine, 10 µg/mL insulin, 10 ng/mL hydrocortisone, 100 units penicillin, 0.1 mg/mL streptomycin and 0.25 µg/mL amphotericin B. The follicles were incubated in 24 well plates (1 follicle/well) at 37° C. in an atmosphere of 5% CO2 and 95% air. Hair follicles were video recorded in the 24-well plates under the dissecting scope under a power of 20×. Typically, initial recordings were made on day 0 (day follicles were placed in culture) or day 1, and again on days 7 or 8. Hair follicle lengths were assessed using an image analysis software system (Computer Eyes and NIH Image).

Inhibition of Human Hair Growth

Human hair follicle growth rate, quantified by hair follicle length, was inhibited in a dose-dependent manner by these agents. Tetramisole caused a 42±5% inhibition of hair growth at a 0.5mM dose, and sodium orthovanadate caused 58±8% reduction in growth rate at a 0.1mM concentration. The results are provided in Table 2.

TABLE 2

| Inhibitor* | Dose (mM) | Hair Follicle Length Increase (mm) Day 6–Day 0) | % Inhibition |
|---|---|---|---|
| Control (for tetramisole) | — | 1.08 ± .25 | 0 |
| Tetramisole | 0.5 | 0.63 ± .06 | 42 ± 5 |
| Control (for sodium orthovanadate) | — | 0.77 ± .09 | 0 |
| Sodium Orthovanadate | 0.1 | 0.32 ± .06 | 58 ± 8 |

Alkaline Phosphatase Activity

Alkaline phosphatase activity was determined using a kit supplied by Sigma Chemical Co. Whole flank organs from hamsters or isolated human hair follicles were homogenized in a Tris-sucrose buffer, pH 7.5, using a polytron. The homogenate was centrifuged at 12,000×g for 5 minutes in a microcentrifuge, and the supernatant was used as the enzyme source. The supernatant (0.1 mL) was added to a reaction mixture containing 0.5 mL substrate (p-nitophenol phosphate) and 0.5 mL reaction buffer (both reagents supplied in the kit). Inhibitors were added in a volume of 0.1 mL. Water was used as a negative control. Reaction mixtures were incubated for 30 minutes at 37° C. The reaction mixtures were then transferred to a tube containing 10 mL 0.05 N NaOH. Absorbance was measured at a wavelength of 410 nm. Concentrated hydrochloric acid (0.2 mL) was added to each tube and tubes were mixed. Again, absorbance was measured at 410 nm. Absorbance values from the second measurement were substrated from the first measurement to give normalized alkaline phosphatase activity. The assay was optimized with respect to protein concentration (linear activity was found between 10 and 100 µg protein/reaction mixture).

It was determined using hair follicle extracts from hamster flank organs that as the total protein added to the enzyme reaction mixture is increased from 0.01 microgram up to 0.1 microgram/reaction the enzyme activity goes up in a linear fashion. Similarly, when the reaction time of the assay is increased from 5 min. to up to 90 min., the product of the enzyme reaction formed goes up linearly.

It also was determined that the follicle enzyme preparations from hamster or human hair follicles when exposed to increasing concentrations of the enzyme inhibitor were inhibited in a concentration dependent manner. Concentration of the inhibitor that results in a 50% reduction in the enzyme activity ($IC_{50}$) was determined from the enzyme activity vs. inhibitor concentration curves. The inhibitor tetramisole produced $IC_{50}$ values of 125 µmolar and 340 µmolar for the hamster hair follicle and the human hair follicle enzymes, respectively. The inhibitor sodium orthovanadate produced $IC_{50}$ values of 40 µmolar and 75 µmolar for the hamster hair follicle and the human hair follicle enzymes, respectively. The results are provided in Table 3.

TABLE 3

|  | $IC_{50}$ (µM) Tetramisole | $IC_{50}$ (µM) Sodium Orthovanadate |
|---|---|---|
| Flank Organ | 125 | 40 |
| Human Hair Follicle | 340 | 75 |

Other embodiments are within the claims.

What is claimed is:

1. A method of reducing mammalian hair growth which comprises selecting an area of skin from which reduced hair growth is desired; and applying to said area of skin a dermatologically acceptable composition comprising an inhibitor of alkaline phosphatase other than cromoglycate or a salt thereof in an amount effective to reduce hair growth.

2. The method of claim 1, wherein the compound is not an inhibitor of mast cell degranulation.

3. The method of claim 1, wherein the concentration of said inhibitor of said composition is between 0.1% and 30%.

4. The method of claim 1, wherein the composition provides a reduction in hair growth of at least 30% when tested in the Golden Syrian hamster assay.

5. The method of claim 1, wherein the composition provides a reduction in hair growth of at least 50% when tested in the Golden Syrian hamster assay.

6. The method of claim 1, wherein the inhibitor is applied to the skin in an amount of from 10 to 3000 micrograms of said inhibitor per square centimeter of skin.

7. The method of claim 1, wherein said mammal is a human.

8. The method of claim 7, wherein said area of skin is on the face of the human.

9. The method of claim 8, wherein the composition is applied to the area of skin in conjunction with shaving.

10. The method of claim 7, wherein said area of skin is on a leg of the human.

11. The method of claim 7, wherein said area of skin is on an arm of the human.

12. The method of claim 7, wherein said area of skin is in an armpit of the human.

13. The method of claim 8, wherein said area of skin in on the torso of the human.

14. The method of claim 8, wherein said human is a woman suffering from hirsutism.

15. The method of claim 1, wherein said hair growth comprises androgen stimulated hair growth.

16. The method of claim 1, wherein the composition further includes a second component that also causes a reduction in hair growth.

17. A method of reducing mammalian hair growth, which comprises
- selecting an area of skin from which reduced hair growth is desired, the area of skin including alkaline phosphatase; and
- inhibiting the alkaline phosphatase sufficiently to cause a reduction in hair growth;
  - wherein the inhibition is not performed by application of cromoglycate or a salt thereof to the area of skin.

18. The method of claim 17, wherein the inhibition is not performed by application of an inhibitor of mast cell degradation to the area of skin.

19. A method of reducing mammalian hair growth, which comprises
- selecting hair follicles from which reduced hair growth is desired; and
- reducing the amount of alkaline phosphatase enzyme protein in the hair follicles sufficiently to cause a reduction in hair growth;
  - wherein the reducing is not performed by application of cromoglycate or a salt thereof to the area of skin.

20. The method of claim 19, wherein said method comprises applying to said area of skin a composition including a dermatologically acceptable vehicle and an agent that binds to alkaline phosphatase messenger-RNA in an amount sufficient to cause a reduction in hair growth.

21. The method of claim 19, wherein the reducing agent is not performed by application of an inhibitor of mast cell degradation to the area of skin.

* * * * *

UNITED STATES PATENT AND TRADEMARK OFFICE
CERTIFICATE OF CORRECTION

PATENT NO.   : 6,299,865 B1
DATED        : October 9, 2001
INVENTOR(S)  : Peter Styczynski and Gurpreet S. Ahluwalia, Ph. D.

It is certified that error appears in the above-identified patent and that said Letters Patent is hereby corrected as shown below:

<u>Title page,</u>
Item [56], References Cited, OTHER PUBLICATIONS, under Cyboron et al., delete "Chemical" and replace with -- Chemistry --.
Insert -- Kailsruhe, STN File Supplier, File Chemical Abstracts, Vol. 112. --.

Signed and Sealed this

Seventh Day of January, 2003

JAMES E. ROGAN
*Director of the United States Patent and Trademark Office*